(12) United States Patent
Quackenbush

(10) Patent No.: US 11,413,381 B2
(45) Date of Patent: Aug. 16, 2022

(54) BREAST PUMP

(71) Applicant: MOMI BRANDS, INC., Winston Salem, NC (US)

(72) Inventor: Carr Lane Quackenbush, Monson, MA (US)

(73) Assignee: MOMTECH INC., Boston, MA (US)

(*) Notice: Subject to any disclaimer, the term of this patent is extended or adjusted under 35 U.S.C. 154(b) by 0 days.

(21) Appl. No.: 17/473,838

(22) Filed: Sep. 13, 2021

(65) Prior Publication Data
US 2022/0031918 A1 Feb. 3, 2022

Related U.S. Application Data

(60) Continuation-in-part of application No. 17/060,302, filed on Oct. 1, 2020, now Pat. No. 11,147,905, and
(Continued)

(51) Int. Cl.
*A61M 1/06* (2006.01)
*A61M 39/24* (2006.01)

(52) U.S. Cl.
CPC ............ *A61M 1/064* (2014.02); *A61M 39/24* (2013.01); *A61M 2205/3344* (2013.01)

(58) Field of Classification Search
CPC ........ A61M 1/06; A61M 1/062; A61M 1/064; A61M 1/066; A61M 1/75; A61J 13/00; A61J 9/00; A61J 9/001
(Continued)

(56) References Cited

U.S. PATENT DOCUMENTS 2,864,628 A 12/1958 Edleson
4,263,912 A 4/1981 Adams
(Continued)

FOREIGN PATENT DOCUMENTS

CA 2240268 A1 12/1999
WO 2004058330 A1 7/2004

OTHER PUBLICATIONS

PCT Application No. PCT/US2017/68633, International Search Report and Written Opinion dated Mar. 19, 2018.
(Continued)

*Primary Examiner* — Scott J Medway
(74) *Attorney, Agent, or Firm* — Lathrop GPM LLP; Wm. Tucker Griffith

(57) ABSTRACT

A breast pump device and associated methods for extracting breast milk ate disclosed. A pump head comprises an external shell with an elastic membrane disposed and bonded therein to define at least one hermetically sealed chamber. Manipulation of the elastic membrane, for example, by adjusting suction or pressure in the sealed chamber or within an interior volume defined by the elastic membrane permits radial mechanical compression (positive pressure) to be applied to a nipple positioned in the pump head to simulate compression of the nipple by the infant's tongue and simultaneously permits axial hydraulic or pneumatic suction (negative pressure) to be applied to the nipple to simulate the infant's minimum intra-oral vacuum. The breast pump device of the present invention can generate these simultaneous compressions and suctions with a single vacuum source, which may be an electric pump or a hand-operated mechanical pump.

11 Claims, 9 Drawing Sheets

Related U.S. Application Data a continuation-in-part of application No. 17/036,605, filed on Sep. 29, 2020, now Pat. No. 11,116,880, said application No. 17/060,302 is a continuation-in-part of application No. 16/251,198, filed on Jan. 18, 2019, now Pat. No. 10,806,837, which is a continuation of application No. 16/004,742, filed on Jun. 11, 2018, now Pat. No. 10,286,130, which is a division of application No. 15/403,578, filed on Jan. 11, 2017, now Pat. No. 10,016,548.

(60) Provisional application No. 62/927,365, filed on Oct. 29, 2019.

(58) Field of Classification Search
USPC ........................................ 604/73, 74
See application file for complete search history.

(56) References Cited

U.S. PATENT DOCUMENTS

| | | | |
|---|---|---|---|
| 4,607,596 A | | 8/1986 | Whittlestone et al. |
| 4,857,051 A | | 8/1989 | Larsson |
| 4,883,464 A | * | 11/1989 | Morifuki ............... A61M 1/064 604/74 |
| 5,749,850 A | * | 5/1998 | Williams ............... A61M 1/82 604/74 |
| 6,090,065 A | * | 7/2000 | Giles ..................... A61M 1/062 604/315 |
| 6,273,868 B1 | | 8/2001 | Nordvik |
| 6,673,036 B1 | | 1/2004 | Britto |
| 6,749,582 B2 | | 6/2004 | Britto et al. |
| 6,840,918 B1 | | 1/2005 | Britto et al. |
| 6,887,210 B2 | | 5/2005 | Quay |
| 7,101,350 B2 | | 9/2006 | Ytteborg |
| 7,875,000 B2 | | 1/2011 | Krebs et al. |
| 7,988,661 B2 | | 8/2011 | Silver et al. |
| 8,052,635 B1 | | 11/2011 | Kelly |
| 8,118,772 B2 | | 2/2012 | Dao et al. |
| 8,216,179 B2 | | 7/2012 | Bosshard et al. |
| 8,961,454 B2 | | 2/2015 | Chen |
| 10,016,548 B1 | | 7/2018 | Quackenbush |
| 10,286,130 B2 | | 5/2019 | Quackenbush |
| 10,485,908 B2 | | 11/2019 | Mvarez |
| 10,806,837 B2 | | 10/2020 | Quackenbush |
| 11,116,880 B2 | | 9/2021 | Quackenbush |
| 11,147,905 B2 | | 10/2021 | Quackenbush |
| 2002/0198489 A1 | * | 12/2002 | Silver ................... A61M 1/066 604/74 |
| 2004/0158199 A1 | | 8/2004 | McKendry et al. |
| 2005/0154349 A1 | * | 7/2005 | Renz ..................... A61M 1/82 604/74 |
| 2005/0234370 A1 | | 10/2005 | Kobayashi |
| 2006/0106334 A1 | | 5/2006 | Jordan |
| 2007/0060873 A1 | * | 3/2007 | Hiraoka ............... A61M 1/066 604/74 |
| 2009/0062731 A1 | * | 3/2009 | Keyong ................. A61M 1/06 604/74 |
| 2014/0121593 A1 | | 5/2014 | Felber et al. |
| 2014/0288466 A1 | | 9/2014 | Alvarez et al. |
| 2014/0378946 A1 | | 12/2014 | Thompson |
| 2015/0065994 A1 | | 3/2015 | Fridman et al. |
| 2016/0000982 A1 | | 1/2016 | Alvarez et al. |
| 2016/0058928 A1 | | 3/2016 | Nowroozi et al. |
| 2016/0206794 A1 | | 7/2016 | Makower et al. |
| 2017/0312409 A1 | | 11/2017 | Alvarez |
| 2019/0240386 A1 | | 8/2019 | Larsson |

OTHER PUBLICATIONS

N.P.Aleekseev, E.V. Omel'yanyuk, and N.E. Talalaeva, Dynamics of Milk Ejection Reflexes Accompanying Continuous Rhythmic Stimulation of the Areola-Nipple Complex of the Mammary Gland, 2000, Ros. Fiziol, Zhum, im. I.M. Sechenova, vol. 86, No. 6, pp. 711-719 (Year: 2000).

\* cited by examiner

BREAST PUMP

CROSS-REFERENCE TO RELATED APPLICATIONS

This application is a continuation-in-part of U.S. patent application Ser. No. 17/060,302, filed Oct. 1, 2020, which is a continuation-in-part of U.S. patent application Ser. No. 16/251,198, filed Jan. 18, 2019, issued as U.S. Pat. No. 10,806,837. which is a continuation of U.S. patent application Ser. No. 16/004,742, filed Jun. 11, 2018, issued as U.S. Pat. No. 10,286,130, which is a divisional of U.S. patent application Ser. No. 15/403,578, filed Jan. 11, 2017, issued as U.S. Pat. No. 10,016.548, each of which is hereby incorporated by reference in its entirety.

This application is also a continuation-in-part of U.S. patent application Ser. No. 17/036.605, filed Sep. 29, 2020, which claims the benefit of U.S. Provisional Application No. 62/927,365, Filed Oct. 29, 2019, each of which is hereby incorporated by reference in its entirety.

TECHNICAL FIELD OF THE INVENTION

The present invention relates generally to milking and breast pump devices and, more particularly, to breast pumps for lactating females designed to mimic the natural suckling action of an infant during breast-feeding. The present invention has applicability to electric breast pumps and manual breast pumps alike.

BACKGROUND OF THE INVENTION

Newborns and infants experience immediate and long-term benefits from breast milk feeding that are well documented. (See Cunningham A. S., Jelliffe D. B., Jelliffe E. F., Breast feeding and health in the 1980s: a global epidemiological review, *Journal of Pediatrics,* 1991. 118:659-666). These benefits include providing protection against many illnesses caused by allergies, bacteria and viruses, such as stomach viruses, respiratory illnesses, ear infections, meningitis and the like. (See Fallot M. E., Boyd J. L., Oski F. A., Breast-feeding reduces incidence of hospital admissions for infection in infants, *Pediatrics,* 1980, 65:1121-1124). Breast milk feeding also may increase intelligence and fight obesity.

Nursing mothers may desire to impart the above-noted benefits of breast milk to their infant when the two are separated. Additionally, traditional nursing may not be possible, or convenient, at all times and locations. Thus, to extract breast milk to later feed to the infant, nursing mothers can use a breast pump. The extracted breast milk can be fed to the infant using a bottle fitted with an artificial teat. Nature is the design gold standard. Ideally, a breast pump should replicate the action of a nursing infant. So, it is instructive to review research on mother/infant nursing versus the action of various commercial breast pumps and milking machines.

Milk Ejection Reflex (MER) and Breast Pressurization

It is generally accepted that significant milk can be expressed only if there is an adequate milk ejection reflex (MER) and to remove milk in large quantities normally requires an MER, nipple extension and application of vacuum by the infant. Research indicates mechanical stimulation of the areola, presumably by the infant's gums arid tongue brings on repeated MERs. (See N. P. Alekseev, E. V. Omel'yanyuk, et al. (2000) "Dynamics of milk ejection reflex during continuous rhythmic stimulation of areola-nipple complex of the mammary gland," *Rossiiskii Fiziologicheskii Zhurnal Imeni I. M. Sechenova,* 86(6):711-719). However, stimulation of the nipple or the breast proximal to the areola does not cause an MER.

MER initiation is a multi-step sequence. Mechanical stimulation of the areola causes a nerve impulse to the hypothalamus, which causes oxytocin to be released from the pituitary gland into the bloodstream. Oxytocin causes contraction of the starfish-like myoepithelial cells surrounding the alveoli (milk producing sacks) in the breast causing intra-ductal pressure to increase, squeezing the milk forward toward the nipple tip.

Direct measurement shows this pressure to be about 20 ml Hg (Cobo, E., M. M. De Bernal, et al. (1967), "Neurohypophyseal hormone release in the human, II. Experimental study during lactation," *American Journal of Obstetrics and Gynecology,* 97: 519-529). Further evidence of ductal pressure increase following an MER comes from ultrasound images showing the areolar ducts expanding from 1.6 mm before the MER to 2.8 mm after the MER. (See D. T. Ramsay, J. C. Kent, R. A. Owens and P. E. Hartmann, Ultrasound Imaging of Milk Ejection in the Breast of Lactating Women, Pediatrics, 2004:113:361).

Thus, a requirement for milk extraction is that the highly elastic nipple ducts must be expanded by internal pressure from an MER. Without duct expansion suction will collapse the highly elastic nipple ducts, blocking milk transmission.

Oxytocin has a half-life of less than 4 minutes, a very short time. (See G. Rydén and I. Sjöholm, Half-life of oxytocin in blood of pregnant and non-pregnant women, *European Journal of Endocrinology,* 1969, Vol 61:Issue 3; pg. 425-431). This means the MER pressure event lasts only a few minutes, If an infant wants more milk, it must create a new MER to repressurize the system. Oxytocin's short half-life thus creates a pressure control mechanism.

Nipple Structure, Valves within the Nipple

Although the breast is pressurized, the fact that milk does not spray out of the nipple is evidence of normally closed valves between the alveoli and the nipple tip. Ultrasonic imaging and the typical behavior of a nursing breast/nipple give evidence for two normally closed valves within the nipple.

The first, located within the nipple, opens when the nipple is elongated. Evidence for this valve are ultrasonic images showing that after an MER, nipple ducts of the non-nursed nipple are barely visible whereas on the nursing side, with the nipple elongated, the nipple ducts are expanded. Further evidence is the observation that after an MER both breasts are pressurized but the non-nursing breast does not spray, presumably because that nipple is not elongated.

The other valve is a sphincter near the nipple tip. It opens if there is sufficient suction to pull milk through it. Warmth can also relax and open it e.g., the warmth of the infant's mouth or when warm wet towels are used to extract milk in Japanese hand massage.

In nursing, the infant elongates the nipple until the nipple is seated into the downward curve of the hard palate at the back of the infant's mouth. It is reported that this elongation can be two times the rest length of the nipple. (See Smith, W. L., Erenberg, A. and Nowak. A. J. (1988), Imaging Evaluation of the Human Nipple During Breastfeeding, *Am J Diseases in Children.* 142:76-78).

Mechanical Nursing Action by the Infant

After the nipple is extended and an MER is achieved, the nursing cycle begins: The cycle generally comprises the following steps:

1. First, the infant drops its tongue. This increases volume in the back of the mouth. This increases suction and, because the nipple is already fully extended and seated, this volume increase cannot be filled by any further increase of nipple length. Milk flows to fill the increased volume.

2. When sufficient milk has been extracted. The infant stops tongue lowering, then reverses the tongue motion. Maximum suction occurs at the bottom or the stroke and decreases as the tongue moves up.

3. When the tongue is fully up, ultrasound evidence shows that the infant compresses the nipple against the roof of its mouth, squeezing the milk ducts closed which stops flow. (See McClellan, H. L., Sakalidis, V. S., Hepworth, P. R., Hartmann, P. E. and Geddes, D. T. (2010), Validation of Nipple Diameter and Tongue Movement Measurements with B-Mode Ultrasound During Breastfeeding, *Ultrasound in Medicine & Biology,* 36 (11):1797-1807). Swallowing ensues.

In the nursing cycle, the infant compresses the nipple to stop flow so it can swallow without flooding. Nipple compression has an unintended benefit for the mom, it prevents poolinglaccumulation of liquid in the nipple tissue. This painful condition, generally caused when tissue has prolonged exposure to vacuum, is known as edema.

Suction Cycle of the Nursing Infant

Intra-oral vacuum traces measured with a pressure probe in a nursing infant's mouth shows vacuum varying from a maximum of about −180 mm Hg to a minimum of about −50 mm Hg. (D. T. Geddes et. al. (2008), Tongue movement and intra-oral vacuum in breastfeeding infants, *Early Human Development,* 84, 471-477). Ultrasound video studies show milk flowing during the maximum suction portion of the curve. The minimum suction portion of the intra-oral suction curve is presumed necessary to maintain nipple extension to enable milk flow. (Elad et.al. (2014), Biomechanics of milk extraction during breast-feeding, *Proc. Nat'l Academy of Sciences,* 111(14): 5230-5235). Indeed, ultrasonic images of nursing infants (McClellan et.al., 2010) show the nipple tip to vary in length by less than 4 mm between maximum suction (tongue down) and minimum suction (tongue up). This contrasts sharply with nipple length excursions of 15 mm, a 2x length variation, regularly observed with conventional breast pumps cycling between −150 mm Hg and atmospheric pressure. Clearly, −50 mm Hg suction can hold the nipple extended, but returning to atmospheric pressure cannot.

How the infant swallows while maintaining negative oral cavity pressure is not obvious. Physics clearly state that fluid will only move from a region of higher to lower pressure. Therefore, to pull milk from the oral cavity during swallowing there must be another source of vacuum at a higher negative pressure further back in the throat. What this is and how it works is not discussed in the literature.

An Ideal Breast Pump

All current commercial breast pumps. including both manual and electric breast pumps, use vacuum (i.e., negative air pressure) applied to the mother's breast to extract milk. As noted, the use of vacuum to extract breast milk is completely different than the natural suckling action of the infant, in which the infant's mouth is filled only with liquid, and no air. Worse still, conventional breast pumps using only vacuum can cause significant pain to the mother, or even edema in nursing mothers, which inhibits the collection and even production of breast milk.

Therefore, it is desirous to provide an improved approach to breast pumps that more closely mimic the natural suckling action of the infant and does not cause pain or edema.

A breast pump which mimics the natural nursing cycle must be able to duplicate the mechanical action and suction cycles of the nursing infant. This requires mechanisms which can:

1. Bring on an MER to pressurize the breast:
2. Extend the nipple and maintain about 50 mm Hg suction to keep the nipple extended to enable milk flow and for efficient nipple compression;
3. Create suction of about 180 mm Hg to extract milk; and
4. Apply radial (mechanical) compression to the nipple to control nipple edema—this radial (mechanical) compression must be applied simultaneously with the axial (nipple extension) suction of about 50 mm Hg.

In design terms this ability to simultaneously apply positive and negative pressure is the difficult design challenge addressed by the present invention.

DESCRIPTION OF THE RELATED ART

Commercial breast pumps use cyclic vacuum (negative air pressure) applied to the mother's nipple, typically inside a hard, plastic shell, to extract milk. In comparing the required mechanisms for a breast pump, listed above, for mimicking the natural nursing cycle, conventional pumps exhibit the following limitations or drawbacks:

1. All breast pumps can generally bring on an MER to pressurize the breast. Many pumps have a "stimulation phase." For example, pump promotional information claims a 120 cycle/minute stimulation cycle creates the MER. However, this is an inadequate explanation, as early pumps having only an extraction cycle and no stimulation phase are still able to create an MER. A more plausible explanation is that the cyclic vacuum which causes the nipple to elongate and retract by a factor of 2 times, is repeatedly dragging the areola across the inflection between the breast shield funnel and nipple tunnel causing a mechanical stimulation of the areola.

2. All breast pumps can generally extend the nipple and extract milk. None have 50 mm Hg minimum vacuum capabilities. Although this fails to replicate the natural nursing cycle, it may not be important for particular conventional pump designs. Such pumps work and can extract milk, and for the manufacturers, that is sufficient despite not being optimal or efficient.

3. All breast pumps can also generally create suction of about 180 mm Hg to extract milk.

4. None of the conventional breast pumps can apply radial (mechanical) compression to the nipple. This is a major shortcoming of commercial pumps leading to nipple edema which can cause nipples to swell until they completely fill the nipple tunnel, a painful condition, It is also noteworthy that the inward (radial) mechanical compression must occur over a sufficient length of the nipple to squeeze out the excessive accumulation of fluid, This requires that the nipple must be in an elongated state when it is compressed. In the natural nursing cycle, nipple compression occurs when suction is at the minimum (baseline) level, when the infants tongue compresses the nipple against the roof of the mouth. This requires that (axial) nipple elongation must be maintained simultaneously while the nipple is mechanically compressed radially. To design a breast pump that can simultaneously extend and compress the nipple without two separate suction sources is a challenge that has not heretofore been addressed by conventional breast pump designs.

SUMMARY OF THE INVENTION

The present invention provides a breast pump for extracting breast milk from a breast that more closely mirrors the natural suckling action of an infant, including nipple compression. As a result, the present invention improves upon the collection of breast milk generally associated with breast pumps.

The breast pump device in accordance with the present invention generally comprises an expandable and contractable elastic membrane adapted to surround the nipple. The breast pump device as so designed is further capable of applying radial mechanical compression (positive pressure) to replicate compression of the nipple by the infant's tongue and is simultaneously capable of applying axial hydraulic or pneumatic suction (negative pressure) to maintain nipple extension and replicate the infant's minimum intra-oral vacuum. More preferably, the present invention is directed to a breast pump device which can generate these simultaneous compressions and suctions with a single vacuum source, such as an electric pump or a hand-operated mechanical pump. Additionally, the elasticity, expansion and contraction capability of this elastic membrane enables the device to fit a wider range of nipple diameters than conventional breast pumps having nipple tunnels made strictly of hard plastic.

According to embodiments of the present invention, a device for extracting breastmilk from a breast, such as a breast pump, comprises an external shell defining an internal cavity and an elastic membrane disposed in said internal cavity. The external shell includes a neck portion defining a proximal end and a distal end, and a feed channel defined at the distal end of the neck portion. The internal cavity of the external shell is in operative communication with at least one of a suction source or atmosphere via at least one opening in the external shell. The elastic membrane includes a funnel-shaped portion configured to receive and seal against the breast of a user, a neck portion extending from the funnel-shaped portion and defining a proximal end and a distal end adapted to receive and position a nipple of the breast, and narrowing at the distal end to an exit port. The neck portion of the elastic membrane generally fits in the neck portion of the external shell such that the exit port of the elastic membrane is in operative communication with the feed channel. The exterior of the elastic membrane is bonded to the interior of the external shell to form a hermetic chamber between the neck portion of the external shell and the neck portion of the elastic membrane. When the, nipple of the user is positioned in the neck portion of the elastic membrane, an unoccupied volume is defined between the nipple tip and the distal end of the elastic membrane.

In accordance with embodiments of the present invention, a constant suction below atmosphere is applied inside the elastic membrane around and in front of the nipple positioned therein, to extend the nipple towards the distal end of the neck portion of the elastic membrane and to extract breast milk. The elastic membrane is also configured to relax radially outwardly, allowing clearance for the nipple to extend when a suction is, introduced into the hermetic chamber, wherein such suction is generally equivalent to the constant suction applied inside the elastic membrane. Additionally, the elastic membrane is configured to expand radially inwardly when a pressure greater than the constant suction is introduced into the hermetic chamber to compress the elongated nipple to control nipple edema.

In accordance with another aspect of the present invention, an annular diaphragm is positioned between the external shell and the elastic membrane, projecting outwardly from the neck portion of the elastic membrane in a direction generally normal to an axis of the neck portion and being bonded to the interior surface of the external shell to define a first proximal chamber and a second distal chamber, each hermetically enclosed between the external shell and the elastic membrane. The first proximal chamber is in operative communication with at least one of a suction source or atmosphere via at least one opening in the external shell. The second distal chamber allows clearance for proximal distal translation of the distal end of the elastic membrane. In operation, a constant suction below atmospheric pressure is applied inside an unoccupied volume within the neck portion of the elastic membrane to extend the nipple and to extract breast milk. A portion of the elastic membrane of the first proximal chamber is configured to relax radially outwardly, allowing clearance for the nipple to extend when a suction is introduced within the first proximal chamber, wherein said suction is generally equivalent to the constant suction applied inside the elastic membrane. Additionally, the portion of the elastic membrane of the first proximal chamber is configured to expand radially inwardly when a pressure greater than the constant suction is introduced into the first proximal chamber to compress the elongated nipple to control nipple edema. Further, the annular diaphragm is configured to deform distally when pressure greater than the constant suction is introduced into the first proximal chamber, thereby pushing the distal end of the elastic membrane distally to create a squeeze-and-pull action on the nipple positioned within the elastic membrane.

In another aspect of the present invention, the first proximal chamber defined between the external shell, the elastic membrane, and the annular diaphragm may be in operative communication with a source of alternating positive and negative pressure via at least one opening in said external shell. Additionally, a portion of the elastic membrane of the first proximal chamber is configured to relax radially outwardly, allowing clearance for the nipple to extend when a suction below atmospheric pressure is introduced within the first proximal chamber, thereby increasing volume and decreasing pressure in the unoccupied volume within the neck portion of the elastic membrane around and in front of the nipple, to extend the nipple therein and to extract breast milk. Still further, the portion of the elastic membrane of the first proximal chamber is configured to expand radially inwardly when a positive pressure is introduced into the first proximal chamber to compress the elongated nipple to control nipple edema.

In accordance with the present invention, the various chambers formed within the breast pump device may be inflated and deflated with different suction sources alternating with atmospheric pressure or with positive displacement electric or manual pumps capable of exerting alternating positive and negative pressure.

In embodiments of the present invention, the elastic membrane used in the breast pump device is capable of cycling between expanded and contracted states at a rate of 100 to 140 cycles per minute, preferably 120 cycles per minute, during stimulation mode to create a milk ejection reflex, and cycling between expanded and contracted states at a rate of 40 to 80 cycles per minute, preferably 60 cycles per minute, during milk extraction. The duration of the expanded compression cycle is about ¼ of the total cycle.

These and other objects, features and advantages of the present invention will become apparent in light of the detailed description of embodiments thereof, and as illustrated in the accompanying drawings.

DETAILED DESCRIPTION OF PREFERRED EMBODIMENTS

The following descriptions of the figures will convey details of construction and operation of breast pumps in accordance with the present invention.

As described herein, the term "vacuum" is used to connote negative air pressure, i.e., air pressure below atmospheric, whereas "suction" is used to connote negative pressure, i.e., pressure below atmospheric, in air-filled or liquid-filled systems. The term "positive pressure" is used to connote fluid pressure, air or liquid, above atmospheric pressure. "Expandable, Inflate", "inflated", "inflating", or similar terms, are used to connote an increase in size caused by applying positive fluid pressure to a bladder, i.e., pumping fluid into the bladder. "Contractible", "deflate", "deflated", "deflating", or similar terms, are used to connote a decrease in size caused by applying negative fluid pressure to a bladder, i.e., removing fluid from the bladder.

Additionally, the terms "proximal" and "distal" are used in their medical sense and directionally with respect to the user. Thus, the "distal portion" of the pump is farthest from the user. "Bottom", "lower" or "down" are generally used in reference to the orientation illustrated in the figures, which generally correspond to intended orientation of the device in use, and signify a direction toward the milk collection container. Conversely, "top", "'upper" or "up" refer to a direction away from the milk container.

The breast pump device in accordance with the present invention generally comprises an expandable and contractable elastic membrane adapted to surround the nipple and, in operation, mimics the natural suckling action of an infant during breast-feeding. The breast pump device as so designed and described hereinafter is capable of applying radial mechanical compression (positive pressure) to replicate compression of the nipple by the infant's tongue and is capable of applying hydraulic or pneumatic suction (negative pressure) to maintain nipple extension and replicate the infant's intra-oral vacuum for extraction of breast milk. More preferably, the present invention is directed to a breast pump device which can generate these compressions and suctions with a single vacuum source, such as an electric pump or a hand-operated mechanical pump.

Figure 1A:
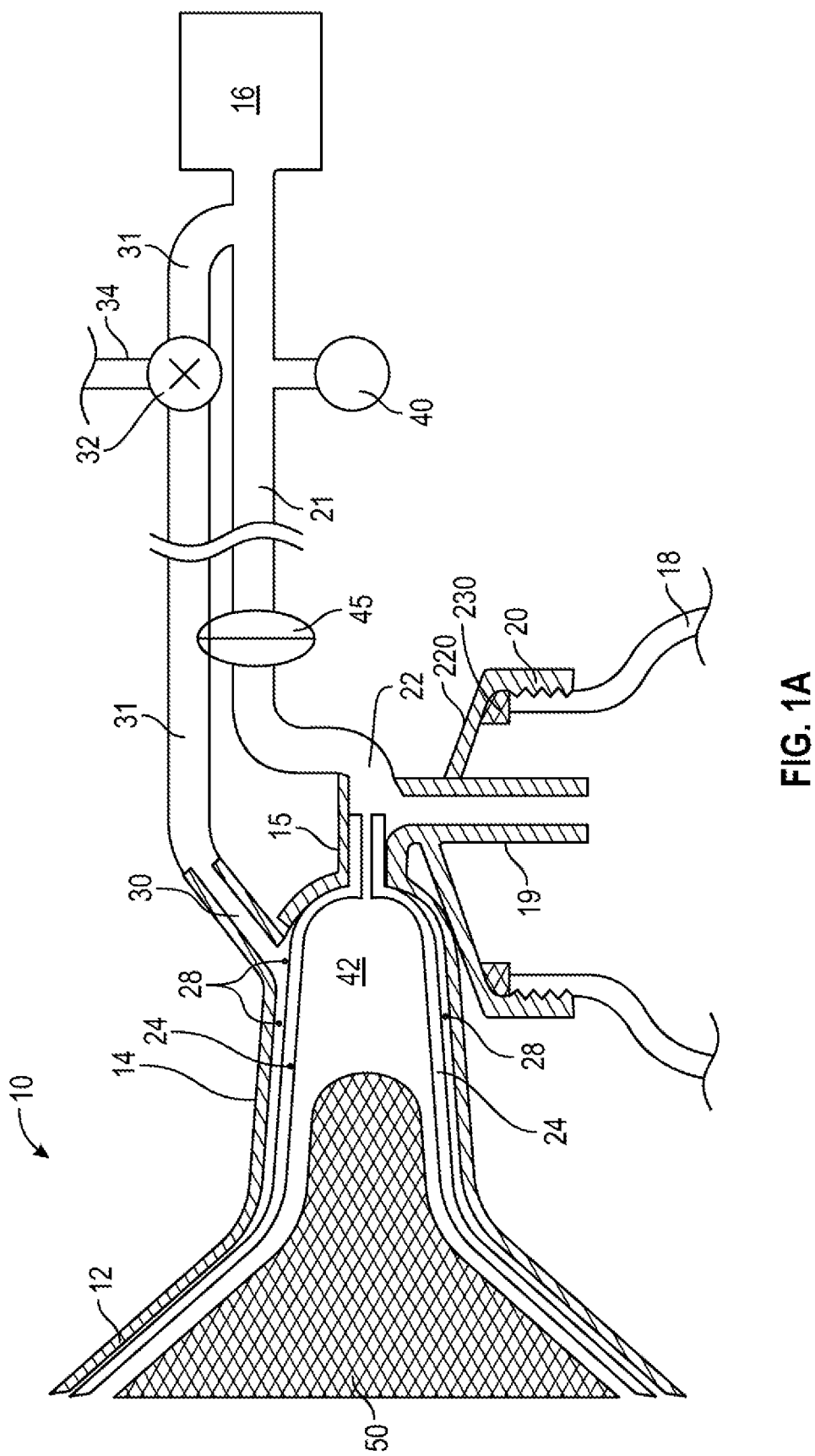
FIG. 1A shows a cross-sectional view of a breast pump in accordance with an embodiment of the present invention, including a 2-tube pump with continuous vacuum to extend the nipple and extract milk and having a 3-way valve enabling atmospheric pressure in to collapse an internal circumferential elastic membrane around the nipple to compress the nipple and thereby control edema.

Referring to FIG. 1A, an assembled breast pump for extracting breast milk in accordance with the present invention is generally designated as reference numeral 10. As shown, the assembled pumping head 10 includes an external hard shell comprising a funnel-shaped breast shield portion 12 adapted to press against a user's breast and which, as illustrated, narrows to a neck portion or nipple tunnel section 14 adapted to receive the nipple 50 of a breast therein for elongation during operation. A feed channel 19 is located at the distal end 15 of the neck portion 14 and leads into a collection container 18, such as a bottle. The collection container 18 is connected to an attachment collar 220 of the pumping head 10 by threads 20 or other suitable connection means known in the art. A seal 230 can be formed between the collection container 20 and the attachment collar 220 to prevent leakage of collected breast milk, or in certain embodiments described herein, to prevent deterioration of suction within the breast pump device.

Still referring to FIG. 1A, a port 22 at the distal end 15 of the neck portion 14 leads through tubing 21 to a vacuum pump 16. A media separation device 45 may be disposed along tubing 21 between the port 22 at the distal end 15 of the neck portion 14 and the vacuum pump 16. The purpose of the media separation device 45 is to prevent milk collected in chamber 42 from entering the vacuum pump 16. In addition, the seal 230 is provided between the attachment collar 220 and the collection container 18 to make the chamber 42, the feed channel 19, the interior of the collection container 18 and the tubing 21 leading to the vacuum pump 16 into a single hermetic unit.

An elastic or elastomeric membrane 24 is disposed inside the external hard shell, and generally runs from within the proximal end of the funnel-shaped breast shield section 12 through the neck portion 14 and into the distal end 15 of the neck portion 14. Preferably, the exterior of the elastic membrane is bonded to the interior of the of the external shell to form a hermetic chamber between the external shell and the elastic membrane 24, For example, as illustrated in FIG. 1A, the elastic membrane 24 is bonded to the inside surface of the funnel-shaped breast shield section 12 and is also bonded to the inside surface of the distal end 15 of the neck portion 14. Thus, bonded at both proximal and distal ends, the elastic membrane 24 forms a hermetic, toroidal, roughly tubular, chamber 28 located between the inside surface of at least the neck portion 14 of the external hard shell and the outside surface of a corresponding neck portion of the elastic membrane 24.

In preferred embodiments, the elastic membrane 24 is constructed of elastomeric materials selected from the group consisting of silicone rubber, thermoplastic elastomer (TPE), latex and the like.

A second port 30 leads out of the hermetic toroidal roughly tubular chamber 28 through tubing 31 to a 3-way valve 32 which can connect the chamber 28, through port 30 and tubing 31, to either atmosphere 34 or to the vacuum pump 16.

The space inside the elastic membrane 24 forms another chamber 42 which is contiguous with the feed channel 19 and with port 22 which leads to the vacuum pump 16. A pressure sensor 40 monitors output pressure of the vacuum pump 16, as well as the pressure in tubing 21 and in the internal chamber 42. Similarly, when the 3-way valve 32 connects the chamber 28 to the pump 16 via tubing 31, the pressure sensor 40 will also monitor pressure in tubing 31 and the chamber 28.

Figure 1B:
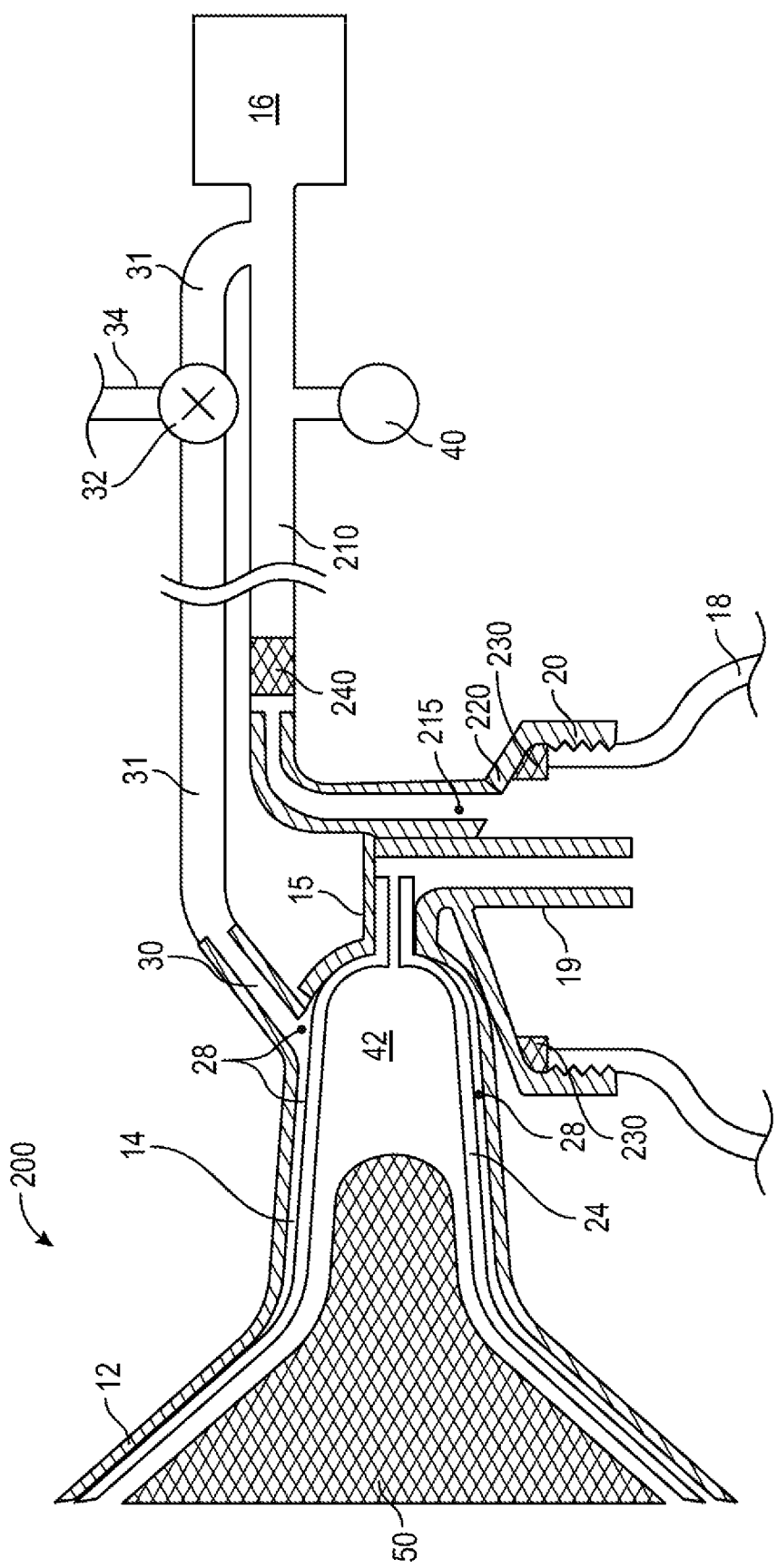
FIG. 1B shows a cross-sectional view of a breast pump in accordance with an alternate embodiment of the present invention, also including a 2-tube pump with continuous vacuum to extend the nipple and extract milk and having a 3-way valve enabling atmospheric pressure in to collapse an internal circumferential membrane around the nipple to compress the nipple and thereby control edema. The vacuum pump evacuates a collection container eliminating need for a media separator.

Referring to FIG. 1B, an assembled breast pump for extracting breast milk in accordance with an alternate embodiment of the present invention is generally designated as reference numeral 200. The illustrated pumping head cross section 200 of FIG. 18 is generally the same as the pumping head 10 disclosed in FIG. 1A. Like components are designated by like reference numerals. In the embodiment of FIG. 1B, the vacuum pump 16 evacuates the collection container 18 so said container 18 acts as a pressure reservoir and a pressure ballast to stabilize pressure fluctuations in chamber 42. To accommodate this change, the vacuum pump 16 is connected through tubing 210 to an intake port 215 on the top distal side of the attachment collar 220 that attaches the pumping head 200 to the collection container 18. In addition, the seal 230 is provided between the attachment collar 220 and the bottle 18 to make the chamber 42, feed channel 19, the interior of the collection container 18 and the tubing 210 leading to the pump 16 into a single hermetic unit. In the configuration of FIG. 1B, breast milk exits the feed channel 19 and falls into the collection container 18; this gives significant physical separation between the milk stream, the milk surface in the collection container 18 and the intake port 215. This separation will help prevent aspiration of milk into tubing 210 and from it into the pump 16. Decreased aspiration risk will eliminate the need for the media separator 45 illustrated in FIG. 1A, a significant simplification. A simple in-line filter 240 may be needed to collect moisture from the warm breast milk and prevent it from condensing in tubing 210.

The pumps 10 and 200 of FIGS. 1A and 1B are 2-tube pumps which operate under continuous vacuum. In operation, a breast and nipple 50 are inserted into the pumping heads, as illustrated. Next, the vacuum pump 16 is switched on with the on/off switch 710 disposed on the control panel, as illustrated in FIG. 3A. In FIG. 1A, the pump 16 evacuates the chamber 42 in the breast pump 10. In FIG. 1B. the pump 16 evacuates the collection container 18, and then the chamber 42. Vacuum in chamber 42 is monitored by pressure sensor 40 and held constant by the control electronics at the level chosen by the user.

At start up, the control software and electronics 780 start an MER sequence by cycling the 3-way valve 32, causing it to connect chamber 28 alternately between pump vacuum and atmospheric pressure at about 100 to 140 cycles/minute, preferably 120 cycles/minute. Duration of the atmospheric portion of each cycle is about ¼ of the total cycle time. As the 3-way valve 32 cycles, the elastic membrane 24 relaxes radially outwardly—i.e., away from the axis of the neck portion of said elastic membrane 24 when suction applied is on both sides. The nipple elongates under suction in chamber 42. When under atmospheric pressure, elastic membrane 24 collapses around the nipple, mechanically compressing it and allowing it to elastically retract. This cyclic elongation and retraction will repeatedly drag the areola across the inflection between the breast shield funnel portion 12 and neck portion 14 causing a mechanical stimulation of the areola. This is presumed to bring on an MER.

Elongation of the nipple will displace air in front of the nipple, in an unoccupied volume within the elastic membrane 24 between the nipple tip and the distal end of said elastic membrane 24, allowing the displaced air to be removed by the vacuum pump 16.

In preferred operation, the MER stimulation phase ends after expiration of a set time (e.g., two minutes) or by the user pressing the MER button 730 on the control panel. The MER button 730 is a toggle, which may be selected any time during the pumping session causing a change from MER stimulation cycle to milk extraction cycle or vice versa. After the end of the MER stimulation phase, the milk extraction mode starts. Milk extraction cycling is between 40 and 80 cycles/minute, preferably 60 cycles/minute.

Milk extraction suction is set by the user using the +/− buttons on the control panel and can vary from about −50 to −250 mm Hg. In milk extraction mode, the nipple extends and milk flows under constant suction from the vacuum pump 16 from the nipple into feed channel 19 then into the collection container 18. Suction is cyclically interrupted when the 3-way valve 32 allows atmospheric pressure into chamber 28 causing the elastic membrane 24 to collapse radially inwardly around the elongated nipple compressing it for the control of edema.

Figure 1C:
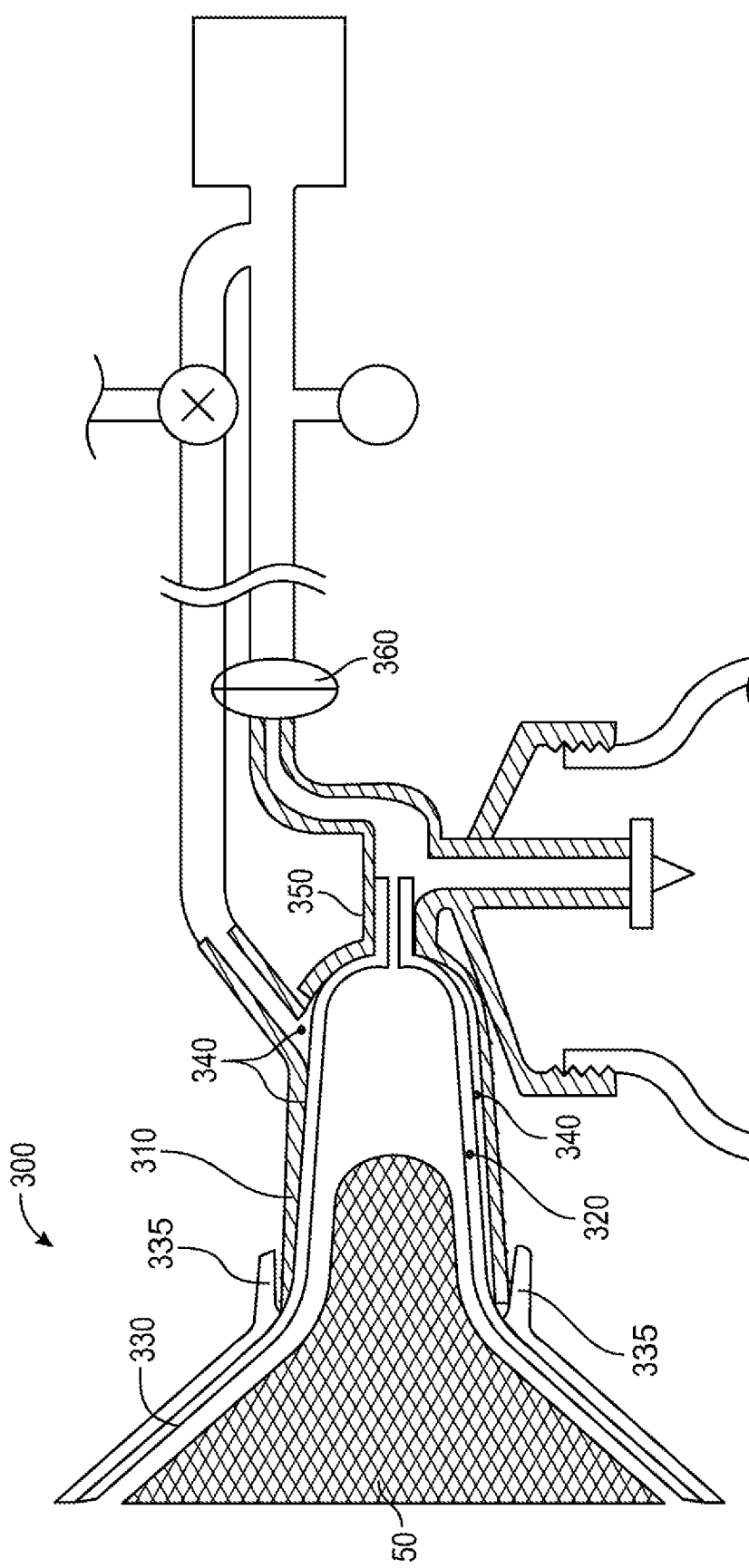
FIG. 1C shows a cross-sectional view of a breast pump in accordance with an alternate embodiment of the present invention, also including a 2-tube pump with a flexible funnel and a different attachment/seal between the external shell and the flexible elastic membrane.

Referring to FIG. 1C, an assembled breast pump for extracting breast milk in accordance with an alternate embodiment of the present invention is generally designated as reference numeral 300. The illustrated pumping head cross section 300 of FIG. 16 is generally the same as the pumping heads 10 and 200 disclosed in FIGS. 1A and 1B, respectively. In the embodiment of FIG. 1C, the funnel-shaped portion of the external shell (portion 12 illustrated in FIGS. 1A and 1B) is eliminated proximally from where it narrows to the nipple tunnel section 310. Instead, in the FIG. 1C configuration, a tubular elastic membrane 320 forms a funnel-shaped portion of the breast shield 330. To form a sufficient attachment and seal between the external hard shell of the neck portion 310, the tubular neck portion 320 of the elastic membrane and the funnel-shaped portion 330 of the elastic membrane/breast shield, a ring-shaped feature 335 is included on the tubular elastic membrane 320. This ring feature 335 extends distally from the outside surface of elastic membrane 320 and makes a hermetic seal with the proximal end of the external shell of the neck portion 310.

As in the embodiments of FIGS. 1A and 1B, the distal end of the elastic membrane 320 is bonded to the inside surface of the distal end 350 of the neck portion 310 of the external shell. Thus, bonded at both proximal and distal ends, the elastic membrane 320 of FIG. 1C forms a hermetic roughly tubular toroidal chamber 340 located between the inside surface of the neck portion 310 of the external shell and the outside surface of the neck portion of the elastic membrane 320.

As in the embodiment of FIG. 1A, a media separation device 360 may be disposed along tubing between the exit port at the distal end 350 of the neck portion 320 and the vacuum pump 16.

This design feature, utilizing the flexible funnel shape portion of the elastic membrane, can be applied to any pump embodiment disclosed in the present invention having a bonded distal end—i.e., the pumps 10 and 200 of FIGS. 1A and 1B without departing from the spirit and principles of the present invention.

Figure 2A:
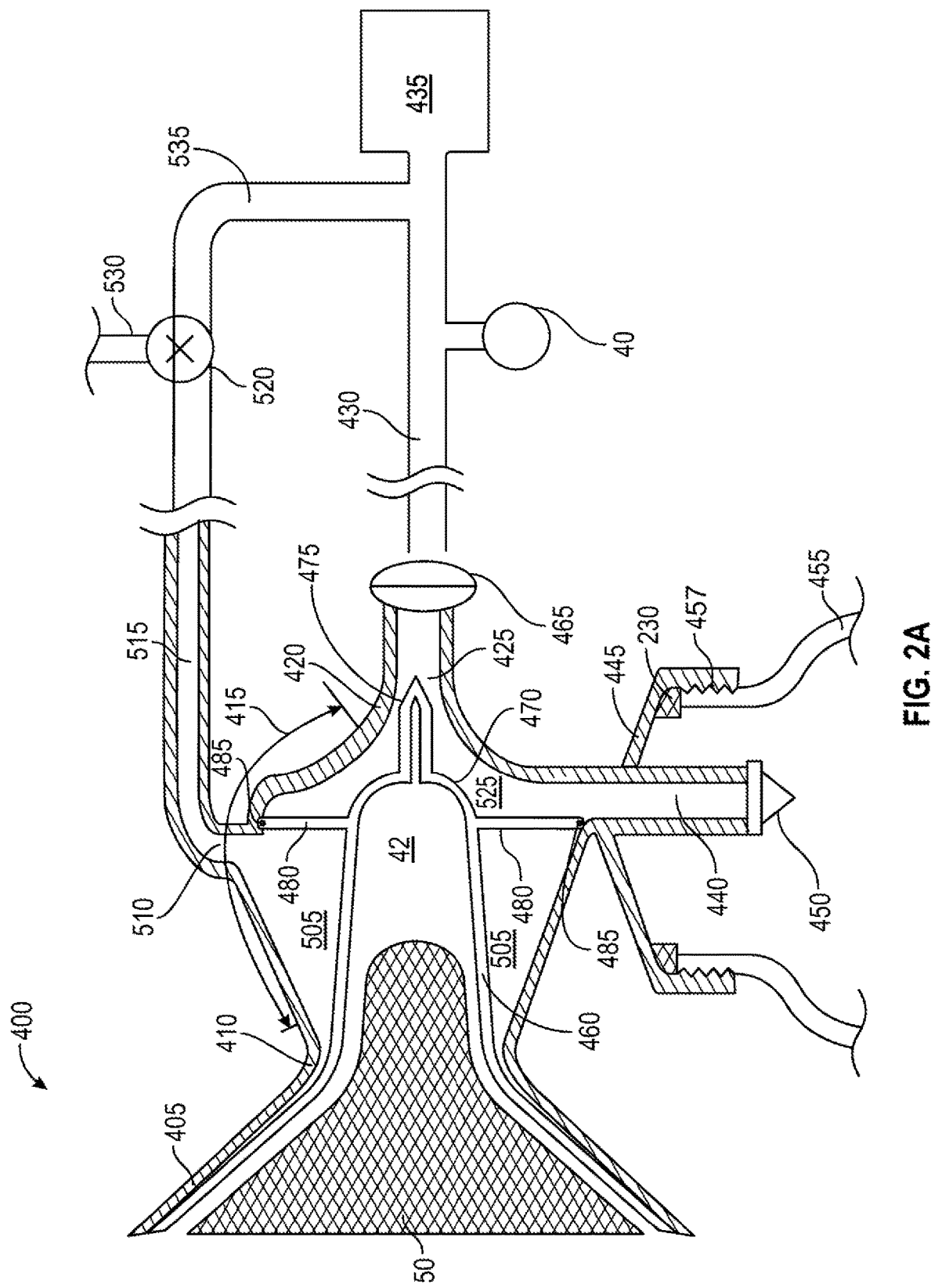
FIG. 2A shows a cross-sectional view of a breast pump in accordance with an alternate embodiment of the present invention, including a 2-tube pump with continuous vacuum to extend the nipple and extract milk and having a 3-way valve enabling atmospheric pressure in to collapse an internal circumferential membrane around the nipple to compress the nipple and thereby control edema. This embodiment also has a pumping section to ensure air or milk is transported from a chamber in front of the nipple into the collection container. It applies a squeeze-and-pull action to the nipple. This design has a media separator.

Referring to FIG. 2A, an assembled breast pump for extracting breast milk in accordance with an alternate embodiment of the present invention is generally designated as reference numeral 400. As shown, the assembled pumping head 400 includes an external hard shell comprising a funnel-shaped breast shield portion 405 which, as illustrated, narrows to a transition portion 410 which then flares out to a circumferentially expanded neck portion or nipple tunnel section 415 which finally narrows to a distal portion 420 where an evacuation port 425 and tubing 430 connecting the interior of the external shell with a vacuum pump 435. As further shown, the bottom of the expanded shell neck portion 415 includes a feed channel 440 leading into a collection container 455. A check valve 450 is disposed between the feed channel 440 and the collection container 455. In preferred embodiments, the feed channel 440 passes through, and is molded as part of, the attachment collar 445. The collection container 455 is connected to the attachment collar 445 of the pumping head 400 by threads 457 or other suitable means known in the art. A media separation device 465 may be disposed along tubing 430 between the evacuation port 425 and the vacuum pump 435. The purpose of the media separation device 465 is to prevent milk from entering the vacuum pump 435.

Referring again to FIG. 2A, an elastic or elastomeric membrane 460 is disposed inside the external hard shell, and preferably extends from the proximal end of the funnel-shaped breast shield portion 405 through the expanded neck portion 415 and then narrows at a distal end 470, finally terminating with a check valve 475. As shown, a'flexible annular diaphragm is positioned along the neck portion of the elastic membrane 460 between the proximal end and the distal end thereof and radially projects outwardly from the neck portion of the elastic membrane 460 in a direction generally normal to an axis of the neck portion and contacting an interior surface of the neck portion 415 of the external shell to define a first proximal chamber 505 and a second distal chamber 525 each enclosed between the external shell and the elastic membrane 460. The annular diaphragm 480 may be integral with the elastic membrane 460, or alternatively, a separate attachment bonded to the elastic membrane 460. In any event, the annular diaphragm 480 is bonded at its periphery 485 to the inside of the expanded neck portion 415 of the exterior hard shell.

Referring again to FIG. 2A, a port 510 in operative communication with the first proximal chamber 505 exits the expanded neck portion 415 of the external shell and leads through tubing 515 to a 3-way valve 520 which can connect the tubing 515 either to the vacuum pump 435 through tubing 535 or to atmosphere 530.

As noted, this configuration of external shell parts, elastic membrane portions, the annular diaphragm, and check valves shown in FIG. 2A, forms a number of internal, preferably hermetically sealed, chambers between the external shell and the elastic membrane 460. Depending on the pressures applied within each chamber, differential pressures will develop across the elastic membrane surfaces, causing the chambers to inflate or deflate, and the portions of the elastic membrane 460 to move radially outwardly or inwardly accordingly.

Figure 2B:
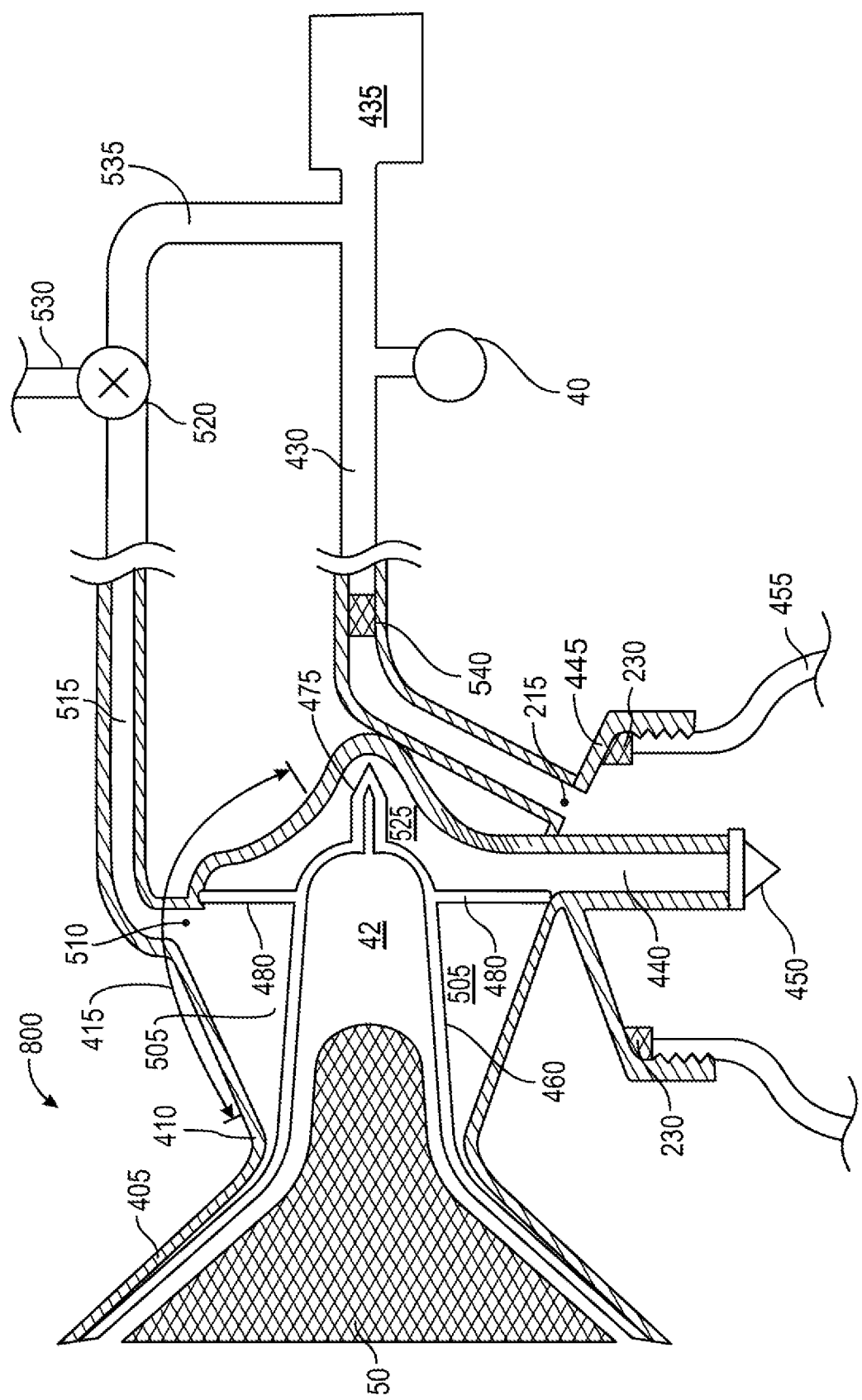
FIG. 2B shows a cross-sectional view of a breast pump in accordance with an alternate embodiment of the present invention, including a 2-tube pump with continuous vacuum to extend the nipple and extract milk and having a 3-way valve enabling atmospheric pressure in to collapse an internal circumferential membrane around the nipple to compress the nipple and thereby control edema. This embodiment also has a pumping section to ensure air or milk is transported from the chamber in front of the nipple into the collection container. It applies a squeeze-and-pull action to the nipple. This design evacuates the collection container and has no media separator.

Referring to FIG. 2B, an assembled breast pump for extracting breast milk in accordance with an alternate embodiment of the present invention is generally designated as reference numeral 800. The illustrated pumping head cross section 800 of FIG. 28 is generally the same as the pumping head 400 disclosed in FIG. 2A. Like components are designated by like reference numerals, In the embodiment of FIG. 2B, the pump 435 evacuates the collection container 455 so it acts as a pressure reservoir and a pressure ballast to stabilize pressure fluctuations in interior chamber 42. To accommodate this change, the pump 435 is connected through tubing 430 to an intake port 215 on the top distal side of an attachment collar 445 that attaches the pumping head 800 to the collection container 455. In addition, a seal 230 is provided between the attachment collar 445 and the collection container 455 to make chamber 42, feed channel 440, the interior of the collection container 455 and tubing 430 leading to the pump 435 into a single hermetic unit.

The pumps 400 and 800 of FIGS. 2A and 2B are 2-tube pumps which operate under continuous vacuum. In operation, a breast and nipple 50 are inserted into the pumping head, as illustrated. Next, the vacuum pump 435 is switched on with the on/off switch 710 disposed on the control panel, generally illustrated in FIG. 3A. In the embodiment of FIG. 2A, the pump 435 evacuates chamber 42 by pulling air through check valve 475. In the embodiment of FIG. 2B, the pump 435 evacuates the collection container 455, and then the chamber 42, by pulling air through check valves 450 and

475. System vacuum levels, including vacuum in chamber 42, are generally monitored by pressure sensor 40 and held constant by the control electronics at the vacuum level chosen by the user.

At start up, the control software and electronics 780 start the MER sequence by cycling the 3-way valve 520, connecting first proximal chamber 505 alternately between pump vacuum and atmospheric pressure at about 100 to 140 cycles/minute, preferably 120 cycles/minute. Duration of the atmospheric portion of each cycle is about ¼ of the total cycle time. As the 3-way valve cycles, the elastic membrane 460 relaxes radially outwardly when suction is on both sides. The nipple elongates under suction in chamber 42. When under atmospheric pressure, the elastic membrane 460 collapses radially inwardly around the nipple mechanically compressing it and allowing it to elastically retract. This cyclic elongation and retraction will repeatedly drag the areola across the inflection between the breast shield funnel and neck portion causing a mechanical stimulation of the areola. This is presumed to bring on an MER.

Elongation of the nipple will displace air in front of the nipple, in an unoccupied volume within the elastic membrane 460 between the nipple tip and the distal end of said elastic membrane 460, allowing the displaced air to be removed by the vacuum pump 435.

In preferred operation, the MER stimulation phase ends after expiration of a set time (e.g., two minutes) or by the user pressing the MER button 730 on the control panel. The MER button 730 is a toggle, which may be selected any time during the pumping session causing a change from MER stimulation cycles to milk extraction cycles or vice versa. After the MER stimulation phase ends the milk extraction mode starts. Milk extraction cycling is between 40 and 80 cycles/minute, preferably 60 cycles/minute.

Milk extraction suction is set by the user using the +/− buttons on the control panel and can vary from about −50 to −250 mm Hg. In milk extraction mode, under constant suction from the vacuum pump 435, the nipple elongates and milk flows from the nipple through check valve 475, into feed channel 440 then through check valve 450 into the collection container 455. Suction is cyclically interrupted when the 3-way valve 520 allows atmospheric pressure into the first proximal chamber 505 causing the elastic membrane 460 to collapse around the elongated nipple compressing it for the control of edema. Introduction of atmospheric pressure into the first proximal chamber 505 also causes the annular diaphragm 480 to deflect distally, for example, when the pressure introduced into the first proximal chamber 505 is greater than the constant suction applied around the elastic membrane 460. This distal deflection will cause an elongation and translation of the distal end of the whole elastic membrane 460. Thus, when atmospheric pressure is let into first proximal chamber 505, the elastic membrane assembly will exert a squeeze-and-pull action an the nipple reminiscent of hand milking.

In the pumps 400 and 800 disclosed in FIGS. 2A and 28, the second distal chamber 525 constitutes a pumping chamber which is in operative communication with check valves 475 and 450. When vacuum is introduced into the first proximal chamber 505, the annular diaphragm 480 will deflect proximally increasing volume and decreasing pressure in the second distal chamber 525. This will cause breast milk to be pumped from chamber 42, inside the elastic membrane 460, through check valve 475 into the second distal chamber 525. Introduction of atmospheric pressure into the first proximal chamber 505 will cause distal deflection of the annular diaphragm 480. This will decrease volume and increase pressure in the second distal chamber 525. This will cause fluid to be pumped from the second distal chamber 525 through check valve 450 into the collection container 455.

A benefit of this pumping action is to reliably move breast milk from the feed channel 440 into the collection container 455 allowing the user to pump in positions other than vertical—e.g., bending over or even lying down. This is not possible with conventional pumps which have only gravity, not pressure, to move milk past the check valve and into the collection container.

In the pump configuration of FIG. 2B, breast milk exits the feed channel 440 and is pumped into the collection container 455. This creates significant physical separation between the milk stream, the milk surface in the collection container 455 and the pump intake port 215. Such separation will help prevent aspiration of milk into tubing 430 and from it into the pump 435. Decreased aspiration risk will eliminate the need for the media separator 465 illustrated in FIG. 2A, a significant design simplification. A simple in-line filter 540 may be needed to collect moisture from the warm breast milk and prevent it from condensing in tubing 430.

Another desirable feature of the pump 800 in FIG. 28 is that the evacuated collection container 455 will act as a vacuum reservoir. Once evacuated, the pump 435 will be very quiet with the only sound being that of the 3-way valve cycling.

Figure 2C:
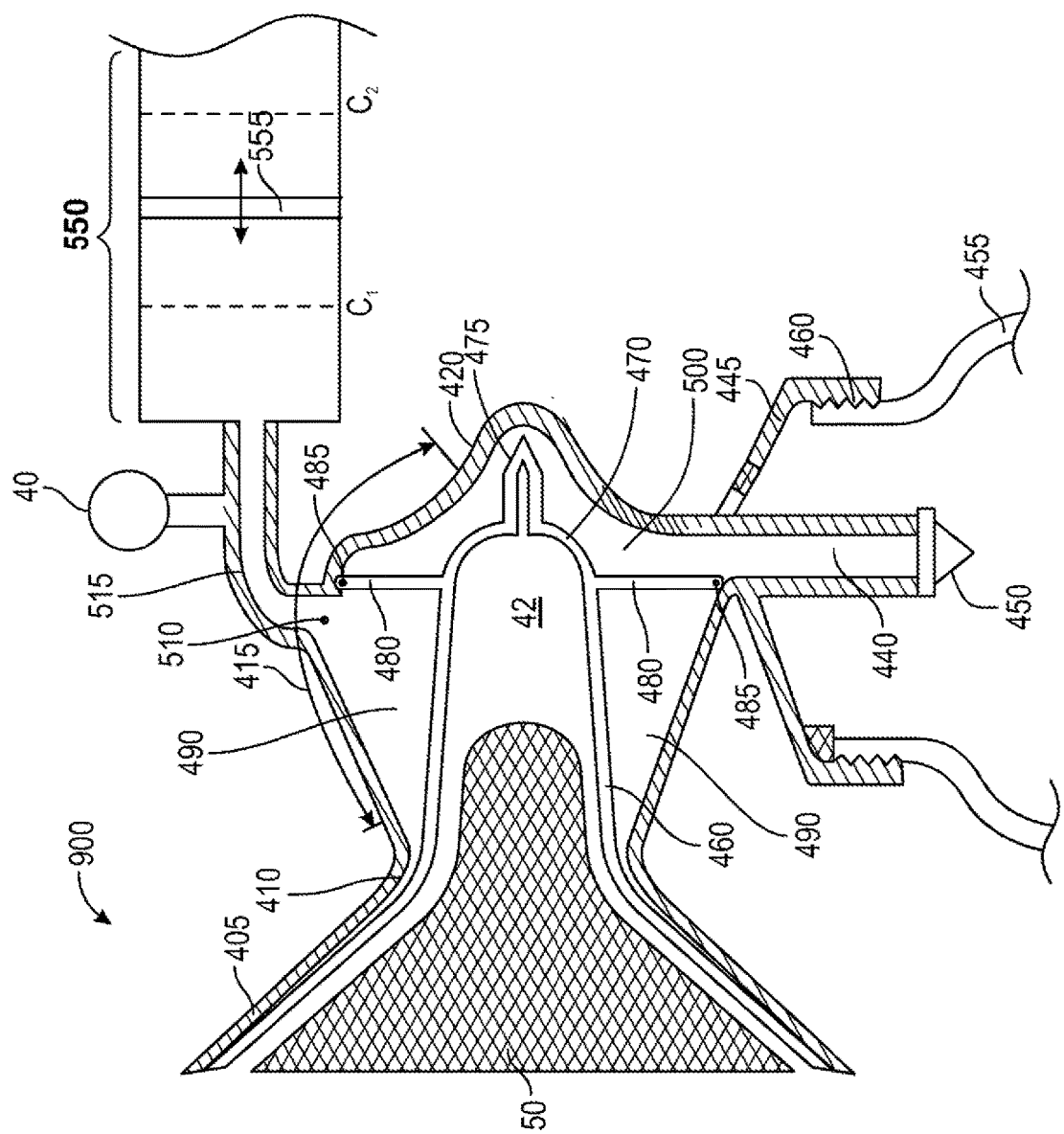
FIG. 2C shows a cross-sectional view of a breast pump in accordance with an alternate embodiment of the present invention, including a 1-tube pump operated by a piston pump capable of exerting negative or positive pressure to an internal circumferential cavity surrounding a tubular elastic membrane which can alternately expand radially outward to create suction to elongate the nipple or extract milk, or the elastic membrane can collapse radially inward, compressing the nipple for control of edema. This embodiment has a pumping section to maintain the nipple extended and to ensure air or milk is transported from the chamber in front of the nipple into the collection container. It applies a squeeze-and-pull action to the nipple, FIGS. 3A and 3B schematically illustrate the layout and internal components of the pump motor and control unit for the electric pumps disclosed herein.

Referring to FIG. 2C, an assembled breast pump for extracting breast milk in accordance with an alternate embodiment of the present invention is generally designated as reference numeral 900. In the embodiment of FIG. 20, a 1-tube pumping head 900 is shown and comprises an external shell comprising a funnel-shaped breast shield section 405 which, as illustrated, narrows to a transition portion 410 which then flares out to an expanded neck portion 415 finally narrowing to a distal portion 420. The external shell includes an evacuation port 510, which is connected to a positive displacement vacuum pump 550 via tubing 515. In FIG. 2C, the vacuum pump is illustrated as a piston pump having a piston 555 that moves between positions $C_1$ and $C_2$. A feed channel 440 is provided at the bottom of the expanded external shell neck portion 415 that leads into a collection container 455. A check valve 450 is disposed between the feed channel 440 and the interior of the collection container 455. In preferred embodiments, the feed channel 440 passes through, and is molded as part of, an attachment collar 445. The collection container 455 is connected to the attachment collar 445 of the pumping head by threads 457 or other suitable means known in the art.

As in the embodiments shown in FIGS. 2A and 2B, the embodiment of FIG. 2C includes an elastic membrane 460 disposed within the external shell. More particularly, the elastic membrane 460 extends from the proximal end of the funnel-shaped breast shield portion 405 through the expanded neck portion 415 and narrows at a distal end finally terminating with a check valve 475. The elastic membrane 460 defines an interior chamber 42 for receiving the user's nipple.

As shown, a flexible annular diaphragm 480 is positioned along the neck portion of the elastic membrane 460 between the proximal end and the distal end thereof and radially projects outwardly from the neck portion 470 of the elastic membrane 460 in a direction generally normal to an axis of the neck portion and contacting an interior surface of the neck portion 415 of the external shell to define a first proximal chamber 490 and a second distal chamber 500, each enclosed between the external shell and the elastic membrane 460. The annular diaphragm 480 may be integral with the elastic membrane 460, or alternatively, a separate attachment bonded to the elastic membrane 460. In any event, the annular diaphragm 480 is bonded at its periphery 485 to the inside of the expanded neck portion 415 of the exterior hard shell.

This configuration of external shell parts, elastic membrane portions, the annular diaphragm 480 and check valves, as shown in FIG. 2C, forms the different chambers: 42, 490 and 500. Depending on the pressures applied within each chamber, differential pressures will develop across the different elastic membrane surfaces, causing membrane portions to move and the chambers to inflate or deflate accordingly.

As noted, the pump 550 of FIG. 2C is a 1-tube, piston pump. In operation, a breast and nipple 50 are inserted into the pumping head 900, as illustrated. Next, the vacuum pump 550 is switched on with the on/off switch 710 disposed on the control panel. At startup, the control software and electronics 780 start the MER sequence by cycling piston 555, for example, between positions $C_1$ and $C_2$. The piston pump starts in MER mode cycling between vacuum and pressure at about 100 to 140 cycles/minute, preferably 120 cycles/minute. Duration of the pressure portion of each cycle is about ¼ of the total cycle time.

When the piston 555 moves from position $C_1$ to position $C_2$, it decreases volume and pressure in the first proximal chamber 490 (which surrounds elastic membrane 460) causing the elastic membrane 460 to move radially outwardly thereby increasing volume and decreasing pressure in internal chamber 42. Decreased pressure in chamber 42 causes the nipple to extend in the previously unoccupied volume, displacing air through check valve 475.

When the piston 555 moves. from position $C_2$ to position $C_1$ it increases volume and pressure in chamber 490, which causes elastic membrane 460 to move radially inward, relieving suction, squeezing the nipple, and allowing the nipple to retract. This cyclic elongation and retraction will repeatedly drag the areola across the inflection between the breast shield funnel and neck portion, causing a mechanical stimulation of the areola. This is presumed to bring on an MER.

In accordance with preferred embodiments, the MER stimulation phase ends after expiration of a set time (e.g., two minutes) or by the user pressing the MER button 730 on the control panel. The MER button 730 is a toggle, which may be selected any time during the pumping session causing a change from MER stimulation cycle to milk extraction cycle or vice versa. After the MER stimulation phase ends the milk extraction phase starts. Milk extraction cycling is between 40 and 80 cycles/ minute, preferably 60 cycles/minute. Milk extraction suction is set by the user using the +/−buttons on the control panel which changes stroke of the piston pump and can vary from about −50 to −250 mm Hg. The pressure sensor 40 monitors system pressure for the control electronics 780 to maintain.

In milk extraction mode, after the nipple is fully extended, breast milk will be extracted from the nipple into chamber 42 when the chamber 42 is under vacuum. This milk will be drawn from the internal chamber 42 into the second distal chamber 500 through check valve 475 only when pressure in the second distal chamber 500 is lower than the pressure in the internal chamber 42. Therefore, as milk is pumped out of the chamber 42, the suction in the second distal chamber 500 must always be greater than in the internal chamber 42. The minimum pressure in the internal chamber 42 is fixed by the elastic retraction force of the nipple. Therefore, suction in the second distal chamber 500 is generally sufficient to keep the nipple extended.

In the pump 550 of FIG. 2C, the second distal chamber 500, working with check valves 475 and 450, constitutes a pumping chamber. When vacuum is increased in the first proximal chamber 490, the annular diaphragm 480 extending between the elastic membrane 460 and the external shell will deflect proximally, thereby increasing volume and decreasing pressure in the second distal chamber 500. This will cause milk to be pumped from the internal chamber 42 through check valve 475 into the second distal chamber 500. When pressure is increased in the first proximal chamber 490, the annular diaphragm 480 will deflect distally decreasing volume and increasing pressure in the second distal chamber 500. This will cause breast milk to be pumped from the second distal chamber 500 through check valve 450 into the collection container 455. A benefit of this pumping action is to reliably move milk from the feed channel 440 into the collection container 455 allowing the user to pump in positions other than vertical—e.g., bending over or even lying down. This is not possible with conventional pumps which have only gravity, not pressure, to move milk past the check valve and into the collection container.

Additionally, when pressure is increased in the first proximal chamber 490, the annular diaphragm 480 will deflect distally and it will stretch the distal end of elastic membrane 460 in the distal direction too. This collapsing and distal translation of the whole elastic membrane 460 will exert a squeeze-and-pull action on the nipple reminiscent of hand milking.

An advantage of the pump 550 disclosed in FIG. 2C is that it comprises a completely closed system, that is, the milk and the working fluid systems are completely separate and so milk cannot contaminate the pump 550.

Figure 3B:
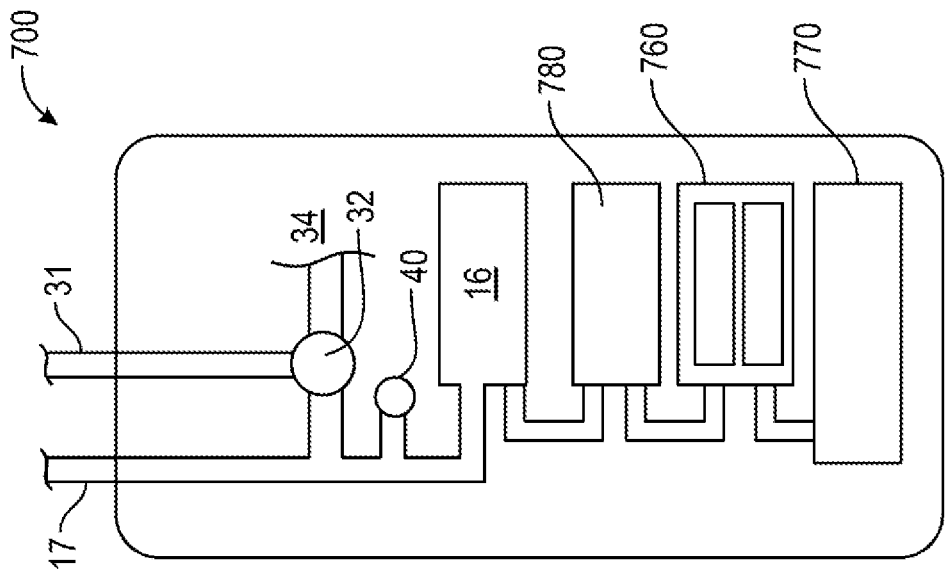
Figure 3A:
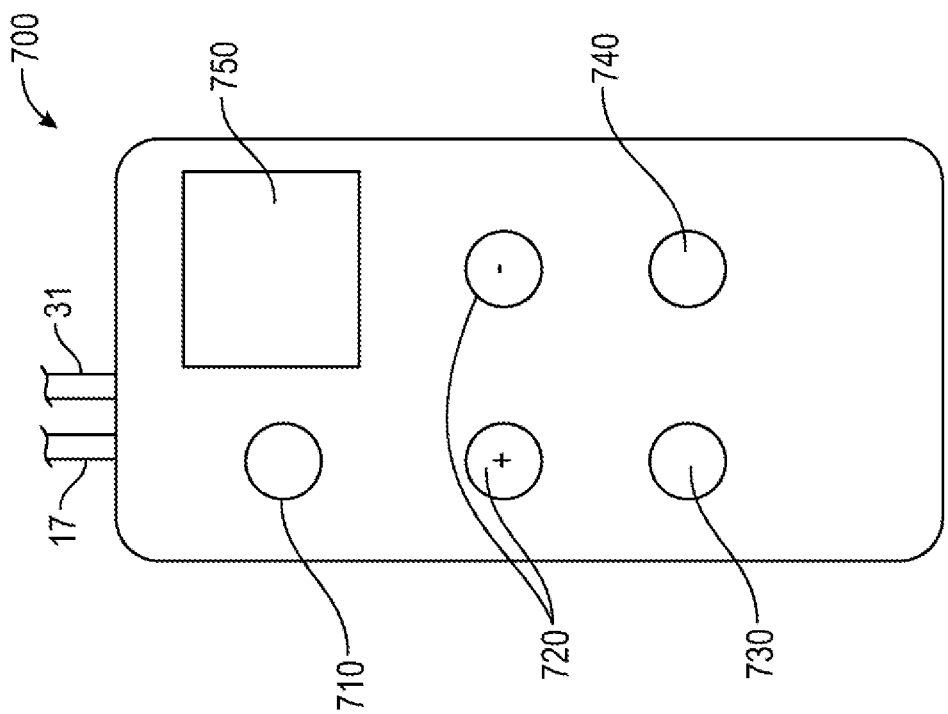

A preferred design for the motor and control unit 700 used to drive any of the electric pump heads disclosed herein is generally illustrated in FIGS. 3A and 3B. As shown, the motor and control unit 700 has two tubes 17 and 31 exiting as needed to drive a single breast shield. If the unit 700 is to power two breast shields, tubes 17 and 31 will each be split to drive the second breast shield.

The exterior of the motor and control unit 700 (FIG. 3A) has different buttons and a visual display. The buttons are, for example: on/off 710, extraction suction up/down buttons 720, MER toggle 730 and a display cycle button 740 that cycles the display for example from extraction pressure to battery charge level to total pumping time. Other buttons or other display items may be added. The motor and control unit 700 may have interact connectivity to allow, for example, connection to cell phone or computer for control of pump operations, logging of data and/or connection to programs for analysis as may be desired by the user.

Internally (FIG. 3B), the suction side of the vacuum pump 16 connects to tube 17 and to the 3-way valve 32 which can connect tube 31 either to the vacuum pump 16 or to atmosphere 34. A pressure sensor 40 monitors output pressure of the pump and in tube 17; and when the 3-way valve 32 connects them, it will also monitor pressure in tube 31.

The vacuum pump 16 is powered by batteries 760 which are monitored and recharged by an AC charging system 770. Software and electronics 780 control the vacuum pump 16 and 3-way valve 31 according to pre-programmed logic and feedback from the pressure sensor 40.

When the pumping session is complete, the on/off switch 72 on control panel 62 is switched to the off position and a shutdown sequence is initiated. The 3-way valve 31 switches to vacuum so all elastic membranes are in their fully retracted position. Control electronics 780 then switch off the vacuum pump and the unit is fully off.

The breast pumps disclosed in FIGS. 1A-2C can be any of a number of positive displacement pumps: diaphragm, piston-driven, peristaltic or the like. Other valving arrangements—e.g., solenoid valves—can functionally replace the 3-way valve.

Breast milk from the collection container can be fed to an infant or stored for future use.

In use, the user can insert a finger into the funnel section of the breast pump head to break any residual vacuum between the breast and the funnel section.

Figure 4:
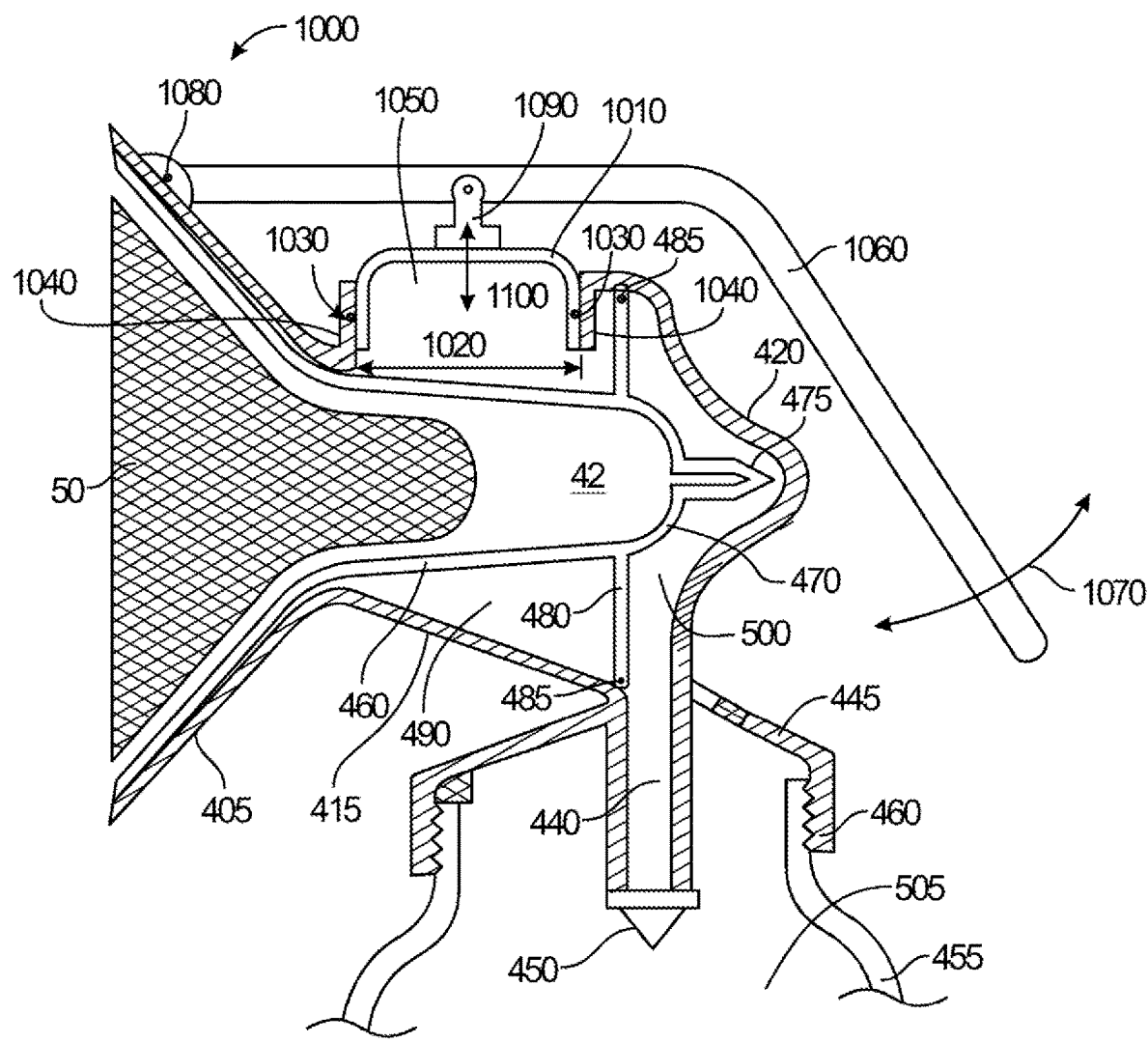
FIG. 4 shows a cross-sectional view of a manual pump in accordance with an embodiment of the present invention that is similar to the pump of FIG. 2C but with an upper diaphragm membrane pump and mechanical actuator replacing the piston pump.

Referring to FIG. 4, an embodiment of a manual breast pump generally designated as reference numeral 1000 is illustrated. The pumping head 1000 of FIG. 4 is generally the same as that illustrated in FIG. 2C except that in the embodiment of FIG. 4, the piston pump 550 depicted in FIG. 2C has been replaced by a deformable upper elastic diaphragm membrane 1010 positioned in an opening or pocket 1020 formed in the expanded neck portion 415 of the external shell whereby the elastic diaphragm membrane 1010 is bonded at 1030 to the inside (as pictured in FIG. 4) or outside of suitably shaped extensions 1040 of the expanded neck portion or nipple tunnel section of the external shell. As so positioned, and bonded, a hermetic capsule is formed among the deformable upper elastic diaphragm membrane 1010, the suitably shaped extensions 1040 of the expanded neck portion, the elastic membrane 460 which is bonded to the funnel-shaped portion 405 of the external shell, the annular diaphragm 480 which at its periphery is bonded at 485 to the inside of the external shell, and the external shell itself.

In embodiments of the present invention, the deformable elastic capsule described above is preferably filled with an incompressible material 1050, such as liquid, gel or the like, but which can also be filled with gas or air.

Alternative designs of such a hermetic capsule as shown and illustrated in applicant's U.S. patent application Ser. No. 17/036,605, issued as U.S. Pat. No. 11,116,880, which is incorporated herein by reference.

In operation, once the breast and nipple 50 are inserted into the pumping head 1000 as pictured in FIG. 4, the handle 1060 of the manual actuator is moved forward and backward by the user (as represented by arrow 1070) causing the handle 1060 to rotate around a hinge pivot 1080 and thereby moving a pushrod 1090 away from or toward the interior axial center of the neck portion 415 (this motion being represented by arrow 1100). The pushrod 1090 is operatively connected, and bonded to, the top surface of the deformable upper elastic diaphragm membrane 1010. Motion of the pushrod 1090 away from the axial center of the neck portion 415 will create negative pressure within the hermetic capsule. This negative pressure will cause the elastic membrane 460 to deform radially outward, away from the axis of the pumping head 1000 thereby creating suction around and in front of the nipple causing the nipple to extend or causing extraction of milk into chamber 42. Negative pressure in the capsule will also cause the annular diaphragm 480 between the elastic membrane 460 and the external shell to deform proximally increasing volume and decreasing pressure in the second distal chamber 500. Decreased pressure in the second distal chamber 500 will cause air, or milk, to move from the interior chamber 42 into the second distal chamber 500 through check valve 475.

Motion of the pushrod 1090 toward the axial center of the neck portion 415 will create positive pressure within the hermetic capsule. This positive pressure will cause the elastic membrane 460 to deform radially inward, toward the axis of the pumping head 1000 compressing the elongated nipple, thereby controlling nipple edema. Positive pressure in the hermetic capsule will also cause the annular diaphragm 480 between the elastomer membrane 460 and the external shell to deform distally decreasing volume and increasing pressure in the second distal chamber 500. Increased pressure in the second distal chamber 500 will cause air, or milk, to move from said chamber 500 into the collection container 455 through check valve 450.

Alternate designs of the mechanical actuation means, to apply pressure to and manipulate the deformable upper elastic membrane 1010, can be used without departing from the principles and spirit of the present invention. For example, additional or fewer linkages can be used to provide the push/pull action. In the alternative, a cable can be connected to either or both the handle 1060 and pushrod 1090 to effectuate deformation of the capsule and thus deformation of the elastomer membrane 460 which surrounds and acts on the nipple.

Additionally, alternate positive displacement pumps to the diaphragm pump pictured in FIG. 4 are possible. For example, a piston/cylinder pump may be used without departing from the principles and spirit of the present invention.

The manual breast pump 1000 of FIG. 4 has the same advantages as the breast pump 900 of FIG. 2C, namely the ability to pump bending over or even lying down and the squeeze-and-pull action.

An additional advantage of the manual pump 1000 in FIG. 4 is that it is a completely closed system, that is, the milk and the working fluid systems are completely separate and so milk cannot contaminate the pump.

All pumps presented in the figures above and described herein, whether powered or manual, meet all requirements of an "ideal" breast pump that mimics the mechanical and suction actions of a nursing infant, as discussed above. Notably, the present invention can (1) bring on an MER to pressurize the breast, (2) extend the nipple and maintain at least about 50 mm Hg suction to keep the nipple extended so milk can flow, (3) create suction of at least 180 mm Hg to extract milk and (4) apply radial (mechanical) compression to the elongated nipple to control nipple edema. This radial (mechanical) compression is applied simultaneously with the axial (nipple extension) suction of at least about 50 mm Hg.

Figure 5A:
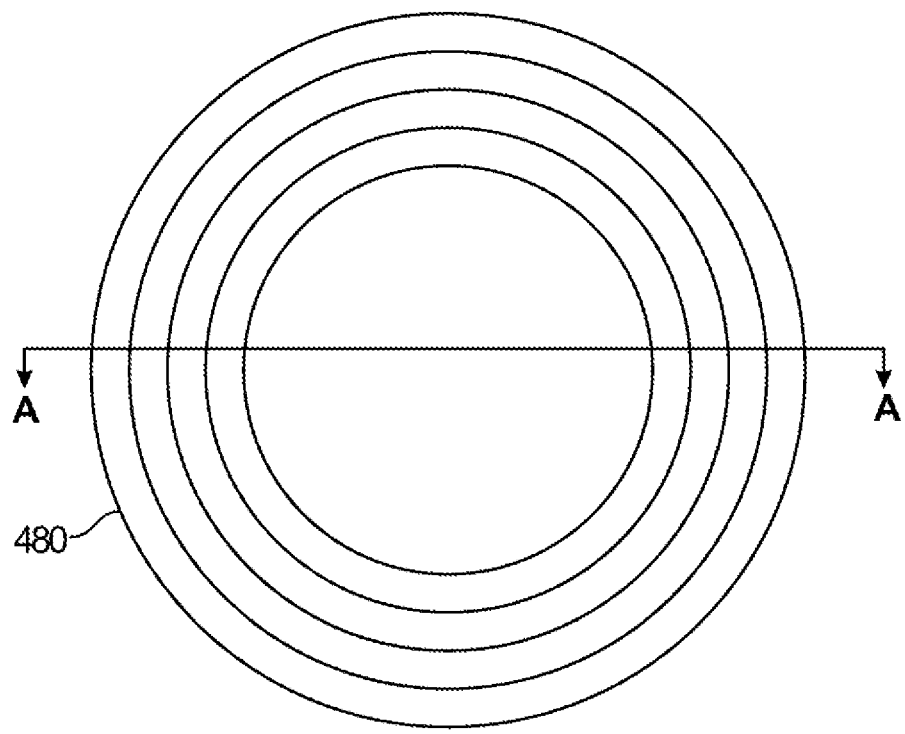
FIGS. 5A and 5B show, respectively, a planar and sectional view of an annular diaphragm which can be used in embodiments of the present invention, extending between the interior elastic membrane and the external shell of the pump. As illustrated, a preferred embodiment of the annular diaphragm includes ribs or ridges to form a shape designed to increase flexibility.
Figure 5B:
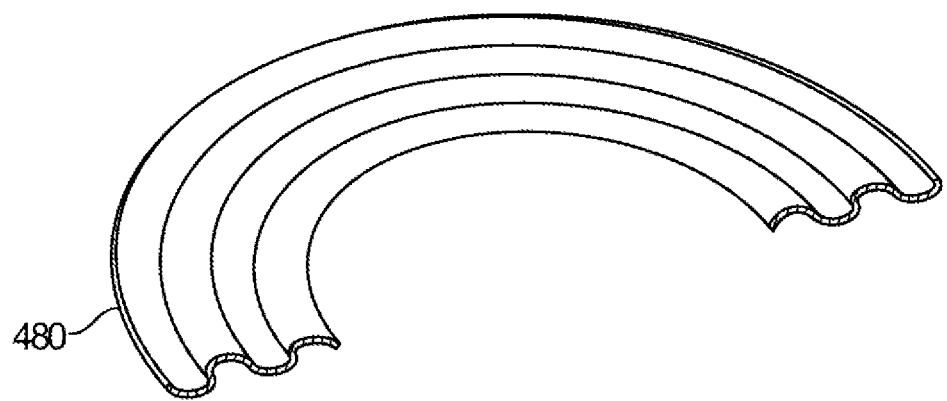

Another embodiment of the present invention is to decrease thickness of, decrease durometer of, or to have a specialty shape for the annular diaphragm 480 positioned on the elastic membrane 460 to increase its flexibility. FIGS. 5A and 5B show a flat annular diaphragm with a ridged, or bellows, shape as one example of a design for the annular diaphragm.

Another embodiment of the present invention provides for self-adjustment or different diameters of nipples. To accommodate different nipple diameters, conventional pumps with hard plastic external shells and no internal elastic membranes are provided in different nipple tunnel sizes. For example, some shells come in up to 5 nipple tunnel diameters ranging between 19 mm to more than 30 mm diameter. The user must choose the appropriate nipple tunnel size based on her nipple diameter. The present invention, utilizing an elastic membrane capable of diameter expansion and contraction enables a single shield to cover a much wider range of nipple diameters. Thus, a single, or just a few different sized flanges are needed.

Although the present invention has been shown and described with respect to the detailed embodiments thereof, it will be understood by those skilled in the art that various changes in form and detail thereof may be made without departing from the spirit and scope of the invention. It is noted that the figures are to be taken as an illustrative example only and are not to scale. Additionally, it is also to be understood that the terminology used is for the purpose of describing particular embodiments only and is not intended to limit the scope of the claims of the present invention.

What is claimed is:

1. A device for extracting breast milk from a breast, said device comprising:
    an external shell defining an internal cavity, said external shell including:
        a neck portion defining a proximal end and a distal end; and
        a feed channel defined at the distal end of the neck portion and including a first check valve; and
    an elastic membrane disposed within the internal cavity of the external shell, said elastic membrane including:
        a funnel-shaped portion configured to receive and seal against the breast of a user;
        a neck portion extending from the funnel-shaped portion and defining a proximal end and a distal end adapted to receive and position a nipple of the breast, said neck portion narrowing at said distal end to a second check valve, wherein said neck portion fits in the neck portion of the external shell such that the second check valve of the elastic membrane is in operative communication with the feed channel, and
    an annular diaphragm positioned along the neck portion between the proximal end and the distal end and radially projecting outwardly from the neck portion of the elastic membrane in a direction normal to an axis of the neck portion and being sealed to an interior surface of the neck portion of the external shell to define a first proximal chamber and a second distal chamber each hermetically enclosed between the external shell and the elastic membrane,
    wherein further, when the nipple of the user is positioned in the neck portion of the elastic membrane, said neck portion defines an unoccupied volume between the nipple tip and the distal end of said elastic membrane;
    wherein the exterior of the elastic membrane is sealed to the interior of the external shell to hermetically enclose the first proximal chamber and the second distal chamber therebetween,
    wherein the first proximal chamber is in operative communication with at least one of a suction source, a positive pressure source, or atmosphere via at least one opening in said external shell,
    wherein the second distal chamber allows clearance for proximal/distal translation of the annular diaphragm and the second check valve therein,
    wherein the elastic membrane is configured to receive a suction pressure below atmospheric pressure that is applied inside the unoccupied volume within the neck portion of the elastic membrane to extend the nipple and to extract breast milk,
    wherein a portion of the elastic membrane of the first proximal chamber is configured to relax radially outwardly, allowing clearance for the nipple to extend when the suction pressure is introduced within the first proximal chamber, wherein said suction pressure is equivalent to the suction pressure applied inside the elastic membrane around and in front of the nipple positioned therein,
    wherein the portion of the elastic membrane of the first proximal chamber is configured to expand radially inwardly when a pressure greater than the first suction pressure is introduced into the first proximal chamber, serving to compress the nipple to control nipple edema, and
    wherein the annular diaphragm extending radially outwardly from the elastic membrane is configured to deform distally when pressure in the first proximal chamber is greater than the pressure in the second distal chamber, thereby pushing the annular diaphragm and the distal end of the elastic membrane distally to create a squeeze-and-pull action on the nipple positioned within the elastic membrane.

2. The device according to claim 1, wherein the feed channel leads into a collection container to receive extracted breast milk.

3. The device according to claim 2, further comprising an attachment portion adapted for connection to the collection container and a seal positioned between the attachment portion and the collection container when connected to one another.

4. The device according to claim 3, wherein a suction device is connected to the device through the attachment portion, whereby said suction device is configured to apply a constant suction to evacuate an interior portion inside the elastic membrane around and in front of the nipple positioned therein, and the collection container.

5. The device according to claim 1, wherein a suction device is connected to the second distal chamber of the device.

6. A device for extracting breast milk from a breast, said device comprising:
    an external shell defining an internal cavity, said external shell including:
        a neck portion defining a proximal end and a distal end; and
        a feed channel defined at the distal end of the neck portion and including a first check valve;
    an elastic membrane disposed within the internal cavity of the external shell, said elastic membrane including:
        a funnel-shaped portion configured to receive and seal against the breast of a user; and
        a neck portion extending from the funnel-shaped portion and defining a proximal end and a distal end adapted to receive and position a nipple of the breast, said neck portion narrowing at said distal end to a second check valve, wherein said neck portion fits in the neck portion of the external shell such that the second check valve of the elastic membrane is in operative communication with the feed channel,
    wherein further, when the nipple of the user is positioned in the neck portion of the elastic membrane, said neck portion defines an unoccupied volume between the nipple tip and the distal end of said elastic membrane; and
    an annular diaphragm positioned along the neck portion between the proximal end and the distal end and bonded thereto and radially projecting outwardly therefrom in a direction normal to an axis of the neck portion to seal to an interior surface of the neck portion of the external shell so as to define a first proximal chamber and a second distal chamber on either side of said annular diaphragm, each said chamber being hermetically enclosed between the external shell and the elastic membrane, wherein the exterior of the elastic membrane is sealed to the interior of the external shell to hermetically enclose the first proximal chamber and the second distal chamber therebetween, wherein the first proximal chamber is in operative communication with a source of alternating positive and negative pressure via at least one opening in said external shell, wherein the second distal chamber allows clearance for proximal/distal translation of the second check valve therein, wherein a portion of the elastic membrane of the first proximal chamber is configured to deform radially outwardly when a suction below atmospheric pressure is introduced within the first proximal chamber, thereby increasing volume and decreasing pressure in the unoccupied volume within the neck portion of the elastic membrane around and in front of the nipple, allowing the nipple to extend and to extract breast milk, wherein the portion of the elastic membrane of the first proximal chamber is configured to expand radially inwardly when a positive pressure is introduced into the first proximal chamber to compress the nipple to control nipple edema, and wherein the annular diaphragm extending radially outwardly from the elastic membrane is configured to deform distally when the positive pressure is introduced into the first proximal chamber, thereby pushing the annular diaphragm and the distal end of the elastic membrane distally to create a squeeze-and-pull action on the nipple positioned within the elastic membrane.

7. The device according to claim 6, wherein the first proximal chamber is filled with one of a liquid, a gel or a gas.

8. The device according to claim 6, wherein the source of alternating positive and negative pressure comprises an electrically-driven positive displacement pump.

9. The device according to claim 6, wherein the source of alternating positive and negative pressure comprises a manually-operated actuating mechanism.

10. The device according to claim 9, wherein the manually-operated actuating mechanism comprises a handle and pushrod assembly which radially deflects the first proximal chamber to exert pressure on the elastic membrane towards or away from the axis of the neck portion.

11. The device according to claim 1, wherein the suction pressure applied inside the elastic membrane may be either constant or cyclic.

* * * * *